(12) United States Patent
Maget (10) Patent No.: US 8,702,915 B2
(45) Date of Patent: Apr. 22, 2014

(54) ELECTROCHEMICAL GAS GENERATOR AND CELL ASSEMBLY

(75) Inventor: Henri Maget, San Diego, CA (US)

(73) Assignee: M & R Consulting Services, Inc., San Diego, CA (US)

( * ) Notice: Subject to any disclaimer, the term of this patent is extended or adjusted under 35 U.S.C. 154(b) by 1166 days.

(21) Appl. No.: 12/413,546

(22) Filed: Mar. 28, 2009

(65) Prior Publication Data

US 2010/0243434 A1 Sep. 30, 2010

(51) Int. Cl.
*C25B 9/08* (2006.01)
*C25B 9/00* (2006.01)

(52) U.S. Cl.
USPC ........... 204/266; 204/252; 204/271; 204/282; 205/633

(58) Field of Classification Search
USPC ................................................. 204/266, 282
See application file for complete search history.

(56) References Cited

U.S. PATENT DOCUMENTS

| | | | |
|---|---|---|---|
| 4,687,423 A | 8/1987 | Maget et al. | |
| 4,886,514 A | 12/1989 | Maget | |
| 4,902,278 A | 2/1990 | Maget et al. | 604/132 |
| 5,242,565 A | 9/1993 | Winsel | |
| 5,681,435 A | 10/1997 | Joshi et al. | 204/266 |
| 5,928,194 A | 7/1999 | Maget | 604/141 |
| 5,938,640 A | 8/1999 | Maget et al. | |
| 5,971,722 A | 10/1999 | Maget et al. | |
| 6,010,317 A * | 1/2000 | Maget et al. | 417/379 |
| RE37,433 E * | 11/2001 | Zimmerman et al. | 205/620 |
| 6,383,165 B1 | 5/2002 | Maget et al. | |
| 6,413,238 B1 | 7/2002 | Maget | |
| 6,780,304 B1 | 8/2004 | Maget | |
| 7,316,857 B1 | 1/2008 | Swanson et al. | |

* cited by examiner

*Primary Examiner* — Bryan D. Ripa
(74) *Attorney, Agent, or Firm* — Steins & Associates, P.C.

(57) ABSTRACT

Small, autonomous, low cost electrochemical gas generators containing an electrochemical cell assembly, a commercially available battery and a current controlling mechanism. Current control, which defines the gas generation rate, is achieved either electronically by means of a resistor or through mass transfer control by means of a gas permeable film of known permeability. In either case, the gas generation rates are generally from 0.1 to 10 cc/day. The gas source must contain an electrochemically active gas such as oxygen or hydrogen. Air is the preferred source for oxygen. These miniature gas generators, generally are less than 1.5 cm in diameter and length, require novel, compact, electrochemical cell assemblies. Various cell assemblies, generally 1 cm in diameter and less than 0.5 mm thick, are described. These miniature gas generators are used for the controlled release of fluids such as pheromones, fragrances, insect repellents, and the like.

19 Claims, 7 Drawing Sheets

ELECTROCHEMICAL GAS GENERATOR AND CELL ASSEMBLY

CROSS REFERENCES TO RELATED APPLICATIONS

None.

STATEMENT REGARDING FEDERALLY-SPONSORED RESEARCH OR DEVELOPMENT

Not applicable.

BACKGROUND

Typical miniature gas sources generate gases at rates from about 0.05 to 100 cc/day and are used for a variety of purposes. A primary use of the gas source is to produce mechanical work, such as may be required for delivering fluids at low flow rates. Many miniature gas sources use chemical means to generate the gases; but these are often unreliable, resulting in time-dependent generation rates.

Another source for generating gases involves the use of an electrochemical means. Electrochemical means to generate gases generally are more accurate, reliable, albeit they require a power source, generally in the form of commercial batteries.

Types of gases generated electrochemically typically include hydrogen, oxygen, and carbon dioxide. In some instances, as described by Winsel in U.S. Pat. No. 5,242,565, the battery is the power source as well as being the hydrogen gas generator. Other examples of electrochemical oxygen generators have been described by Maget in U.S. Pat. No. 6,010,317. Their applications to fluid delivery have also been described by Maget in U.S. Pat. Nos. 4,687,423; 4,886,514; 4,902,278; 5,928,194; 5,938,640; 5,971,722; 6,383,165, and 6,413,238.

Additional examples of electrochemical generators releasing carbon dioxide and hydrogen have been described by Swanson, et. al., in U.S. Pat. No. 7,316,857 and by Maget in U.S. Pat. No. 6,780,304. Setting the gas generation rates of electrochemical generators, however, requires conventional current controllers.

For commercial commodity products, such as releasers of pheromones, fragrances, insecticides, etc., a low cost for the gas generator is of paramount importance. The purpose of the present invention is to describe miniature and autonomous oxygen-gas generators that are cost-compatible with commercial commodity products, and in some instances are low cost gas sources that do not, but could, require electronic controls.

SUMMARY

The above-noted problems, among others, are overcome by the electrochemical gas generator. Briefly stated, the electrochemical gas generator has a unique electrochemical cell assembly generating gases either through a controlled electric current [current-based] or through an oxygen-permeable film of a known permeability [film-based] placed at or near the top of the electrochemical gas generator or the bottom of the electrochemical gas generator. The preferred gas to be generated is oxygen, though other gases may also be generated as necessary.

The electrochemical cell assembly generates gases either through controlled electric current [current-based] or through an oxygen-permeable film of a known permeability [film-based]. Each type of cell assembly has an electrolytic membrane and a catalytically active electrode above and below the electrolytic membrane.

In the current-based type, a conductive and porous current collector is above each electrode and an upper and a lower oxygen-impermeable film encircles and presses onto each current collector thereby forming an air-tight seal therearound. Gases are generated and released based on the current flow when the electrochemical gas generator is activated.

In the film-based type, a conductive and porous current collector is above the upper electrode and an oxygen-permeable film of the conductive type of a pre-determined oxygen permeability is below the lower electrode, and an upper and a lower oxygen-impermeable film encircles and presses onto the upper current collector and onto the oxygen-permeable film thereby forming an air-tight seal therearound. Gases are generated and released based on the oxygen-permeability when the electrochemical gas generator is activated.

The gas generators of this disclosure are small, autonomous, low cost electrochemical gas generators containing, as described above, an electrochemical cell assembly, a commercially available battery, and a current controlling mechanism which defines the gas generation rate and is achieved either electronically by means of a resistor or through mass transfer control by means of a gas permeable film of known permeability. In either case, the gas generation rates are generally from 0.1 to 10 cc/day. The gas source must contain an electrochemically active gas such as oxygen or hydrogen. Air is the preferred source for oxygen. These miniature gas generators, generally are less than 1.5 cm in diameter and length, require novel, compact, electrochemical cell assemblies. Various cell assemblies, generally 1 cm in diameter and less than 0.5 mm thick, are described. These miniature gas generators are used for the controlled release of fluids such as pheromones, fragrances, insect repellents, and the like.

The foregoing has outlined the more pertinent and important features of the electrochemical gas generator in order that the detailed description that follows may be better understood so the present contributions to the art may be more fully appreciated. Additional features of the electrochemical gas generator will be described hereinafter which form the subject of the claims. It should be appreciated by those skilled in the art that the conception and the disclosed specific embodiment may be readily utilized as a basis for modifying or designing other structures and methods for carrying out the same purposes of the electrochemical gas generator. It also should be realized by those skilled in the art that such equivalent constructions and methods do not depart from the spirit and scope of the electrochemical gas generator as set forth in the appended claims.

BRIEF DESCRIPTION OF THE DRAWINGS

For a fuller understanding of the nature and objects of the electrochemical gas generator, reference should be had to the following detailed description taken in conjunction with the accompanying drawings in which.

DETAILED DESCRIPTION

Figure 1A:
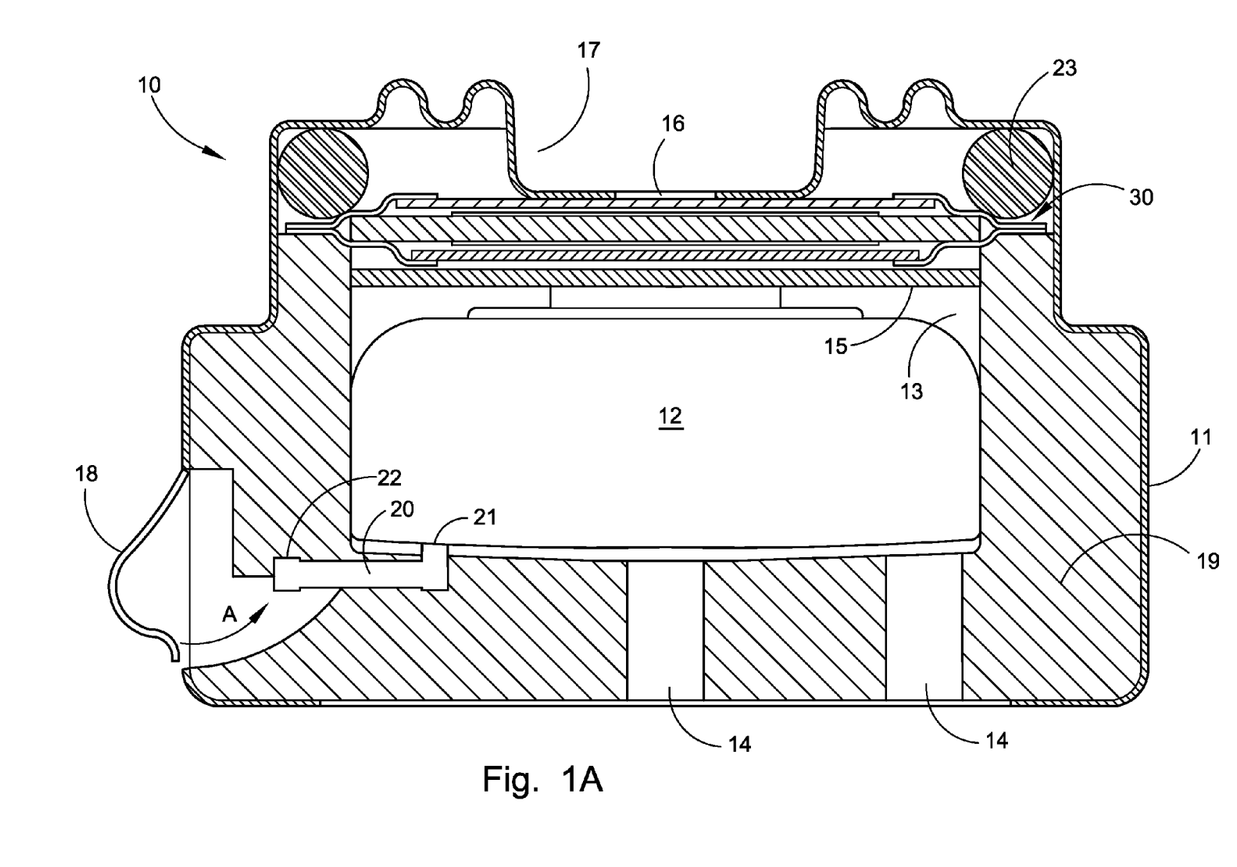
FIG. 1A is a cross-section view of one embodiment of the electrochemical gas generator.
Figure 1B:
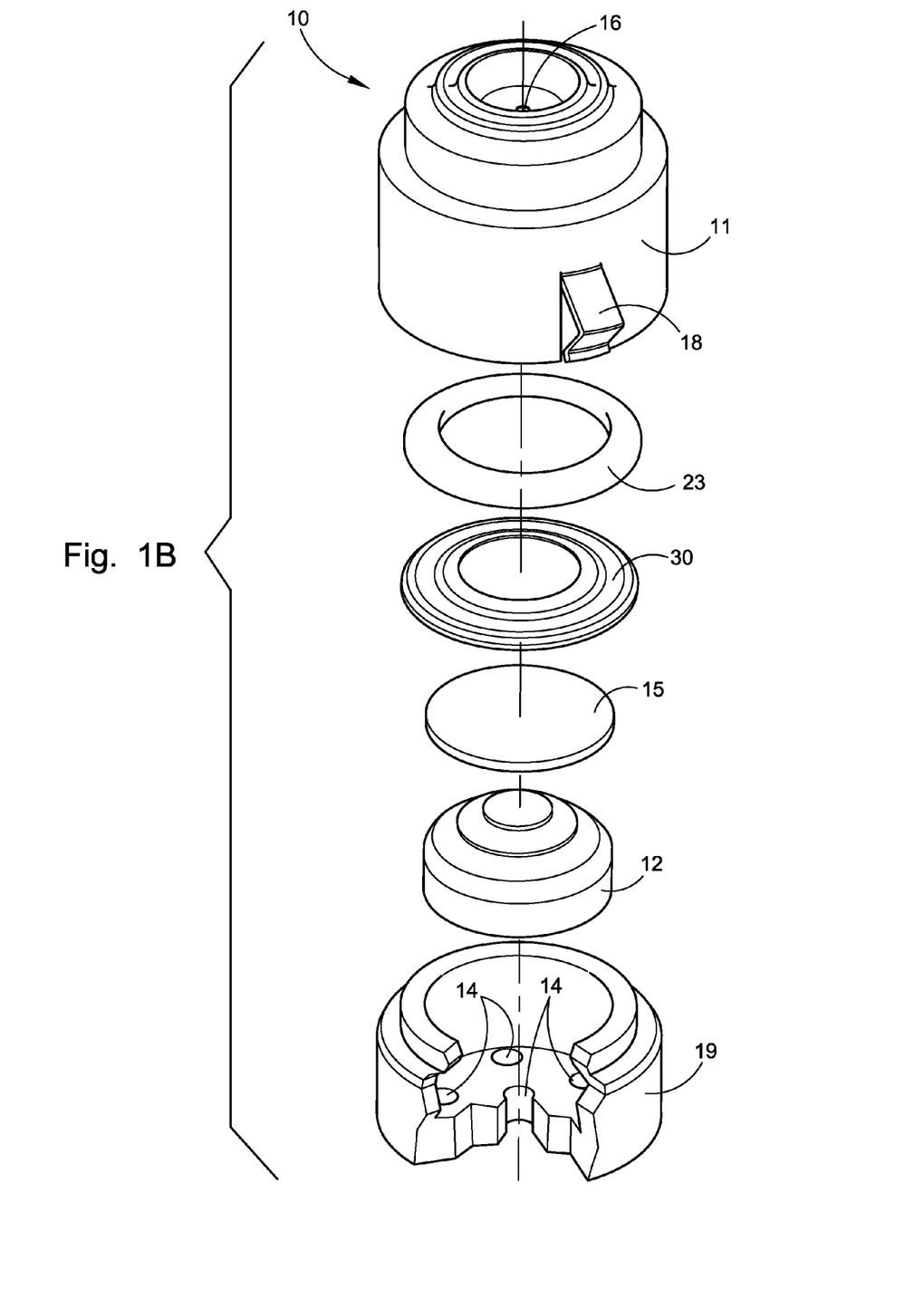
FIG. 1B is an exploded view of the electrochemical gas generator illustrated in FIG. 1A.

FIGS. 1A and 1B are representative of a preferred embodiment of the present miniature and autonomous electrochemical gas generator 10 the gas generation of which is controlled by the simplest form of current controller, a resistor 20 [the gas generated herein typically is oxygen]. It is small, compact, easy to manufacture and assemble, simple to use, efficient, and cost-effective. This particular electrochemical gas generator 10 is of the current-controlled resistor based type in that generation of gases is controlled by a commercial resistor. An important component of this electrochemical gas generator is the electrochemical cell assembly 30. This particular electrochemical cell assembly 30 is illustrated in detail in FIG. 3A and a second embodiment is illustrated in detail in FIG. 3B.

This electrochemical gas generator 10 comprises a container 11 made of conductive material. The container 11 has a chamber 13 therein to accept a battery housing 19, a battery 12, and the resistor 20 with a first contact point 21 in communication with the battery 12 at one end and a second contact point 22 in potential communication with the activation arm 18 at the other end. Activation of this electrochemical gas generator 10 occurs when it is placed into a suitable container having a diameter approximately equal to or slightly greater than the diameter of the electrochemical gas generator 10 which causes the activation arm 18 to move in the direction of Arrow A and thereby come into contact with the second contact point 22 causing the process to begin.

An inlet 14 [one or more for allowing entry of any oxygen-containing gas, such as, but not limited to, air] at the bottom of the container 11 permits the entry of air which will flow around the battery 12 and up to the electrochemical cell assembly 30 where oxygen will be extracted and released through the outlet 16 on top of the on the container 11. Resting on top of the battery 12 in this embodiment is a conductive member 15 generally comprised either of, but not limited to, conductive rubber or a metal screen. The conductive member 15 ensures good electrical contact between the battery 12 and the electrochemical cell assembly 30.

Figure 3A:
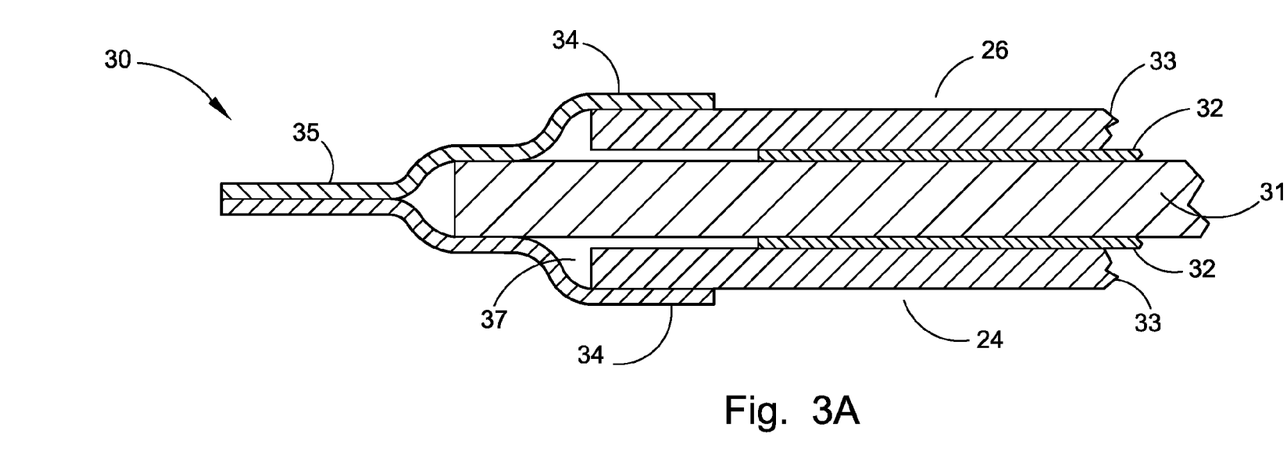
FIG. 3A is a cross-section detailed view of one embodiment of an electrochemical cell assembly which may be film-controlled or current-controlled.

FIG. 3A illustrates in detail the electrochemical cell assembly 30 of this current-based current-controller generator 10. It is composed of a solid electrolytic membrane 31 onto which electrodes 32 are embedded. Current collectors 33 are on the top and bottom of the electrolytic membrane 31 and are in intimate contact with each electrode 32 to insure low resistance electrical contacts. This membrane-electrode/current-collector 31, 32, 33 combination is encircled by, and partially sandwiched between, an oxygen impermeable film 34 which is used to seal off the edges by way of outward extensions 35. As can be seen clearly in FIGS. 3A and 3B, the oxygen impermeable film 34 with the outward extensions 35, in conjunction with the sealing ring 23, will prevent air from circulating around the electrochemical cell assembly 30 but forces the air to flow to the electrochemical cell assembly 30 from its air intake side 24, to be processed, with oxygen being released at the discharge side 26 of the electrochemical cell assembly 30 and out of the electrochemical gas generator 10 through its outlet 16.

The top of the container 11 has a recess 17 which, when assembled with the electrochemical cell assembly 30 inside, presses on the electrochemical cell assembly 30. This maintains a tight fit of the electrochemical cell assembly 30 therein and on the conductive member 15 in tight communication with the top of the battery 12. An air-tight seal is formed to prevent air from flowing around the electrochemical cell assembly 30 and to prevent the generated oxygen to reverse flow and escape to the air intake side 24 of the electrochemical cell assembly 30.

Reference is now made to FIG. 1B for assembly of this current-based electrochemical gas generator 10. First the sealing ring 23 is placed into the inverted housing 11 followed by the electrochemical cell assembly 30, conductive member 15, battery holder 19 with battery 12 and resistor 20 therein. The bottom of the housing 11 is crimped inward and upward. Once so assembled and properly crimped, this electrochemical gas generator 10, when activated becomes operational.

Referring now to FIG. 3A, typical conventionally available components of the electrochemical cell assembly 30 include:

[1] for the resistor [20], a Vishay low-power surface mount chip resistor (see FIG. 1A);

[2] for the electrolytic member (cation or anion) [31], a typical membrane which is manufactured by DuPont® and known as Nafion®;

[3] for the electrodes [32], catalytically active materials such as platinum black or platinum activated carbons or graphite;

[4] for the current collector [33], which typically should be approximately 320 microns thick and less than 5 mm in diameter, porous conductive carbons or graphite paper or porous conductive materials such as conductive silicone rubber or a metal screen; and

[5] for the oxygen impermeable film [34] and outward extensions [35], DuPont's® commercially available Kapton® film which generally should be of the non-conductive type.

As illustrated in detail in FIG. 3A, the oxygen impermeable film 34 and its outward extensions 35 sandwich the membrane-electrode, current-collector combination 31, 32, and 33 and, with the outward extensions 35, prevents air from circulating around the electrochemical cell assembly 30.

There is a substantially wide mouth opening on both the bottom surface and the top surface of the electrochemical cell assembly which defines a respective intake side 24 [bottom] and a discharge side 26 [top]. When the electrochemical cell assembly 30 is combined with the container assembly 11 described above, the air-tight seal described above forces air or any other oxygen-containing gas source to flow to the electrochemical cell assembly 30 from the intake side 24 of the electrochemical cell assembly 30 to be processed, with oxygen being released at the discharge side 26 of the electrochemical cell assembly 30 and out of the electrochemical gas generator 10 through its outlet 16.

Electrochemical oxygen enrichment using air as a source has been previously described in the prior art. The process is typically conducted by applying a voltage across an electrochemical cell consisting of catalytic anode and cathode and an electrolytic member or ionic polymer such as DuPont's Nafion®. Electrode processes are:

Cathodic reduction: $O_2(air) + 4H^+ + 4e^- \rightarrow 2H_2O$

Anodic oxidation: $2H_2O \rightarrow 4H^+ + 4e^- + O_2$

The over-all reaction is: $O_2(air) \rightarrow O_2(pure, compressed)$

The correlation between current and gas generation rate, at 25° C. is 5.5 cc of oxygen/day-mA. Conversely, the amount of energy required to generate 1 cc of oxygen is 4.4 mA-hr. The over-all process can take place at a voltage of less than 1.5 volts and is therefore compatible with most commercial batteries.

The amount of gas generated by batteries such as the 357 silver oxide button cell is ca. 36 cc of oxygen, while the 675 Zinc-air battery can release from 110-140 cc of oxygen. Larger volumes can be produced from commercial alkaline batteries such as AAA and AA.

Since the rates of fluid deliveries of interest to this invention are generally less than 1 mL/day, the applied currents are less than 200 micro-amps. In fact, 20 micro-amps are adequate for delivery rates of 0.1 mL/day. Since air-operated electrochemical cells have a capacity of about 100 mA/cm$^2$, or 550 cc of oxygen/day-cm$^2$, it is apparent that to achieve the desired rates of 1 mL/day or less, the cell size can be extremely small, therefore, non-conventional electrochemical cell assemblies are required as compared to more conventional assemblies such as those described by Maget in U.S. Pat. No. 6,010,317.

Figure 2A:
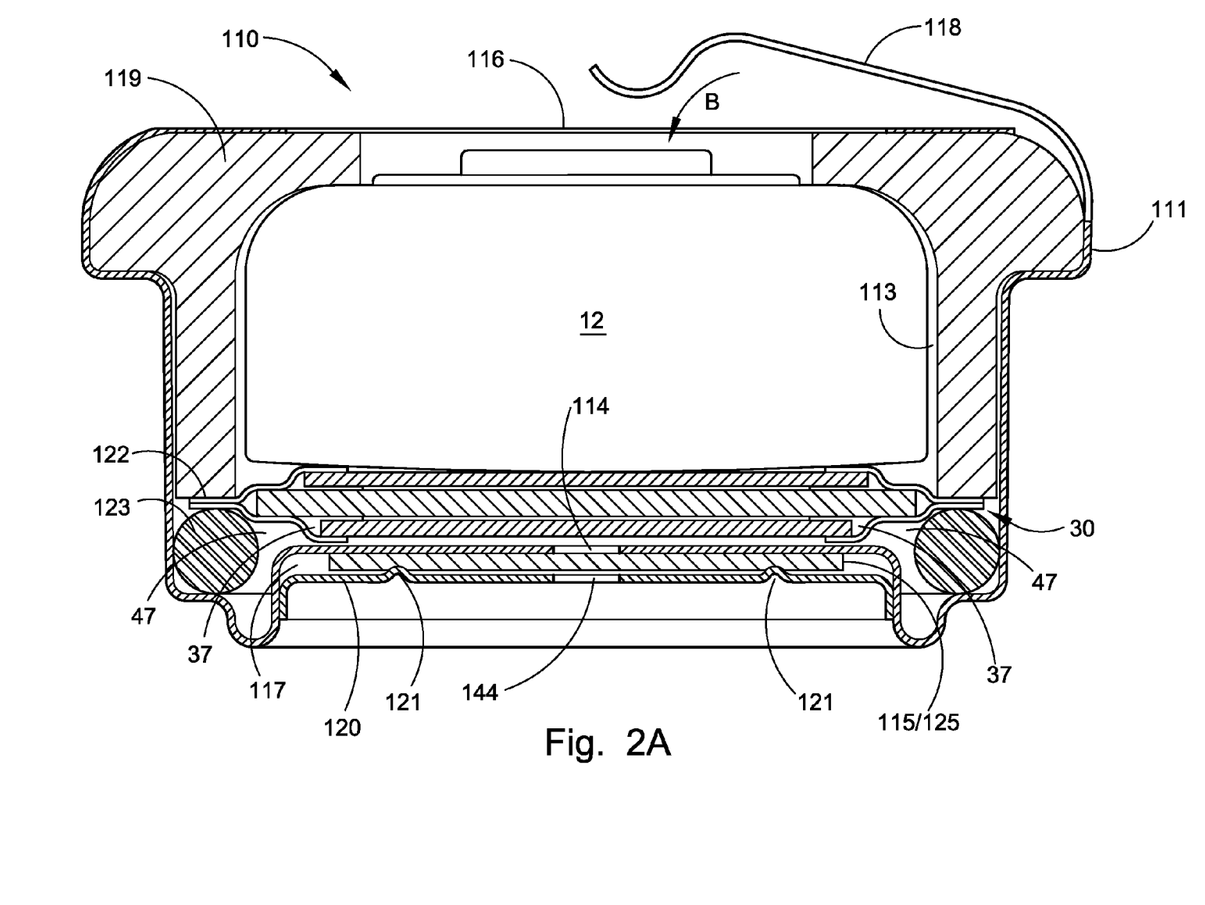
FIG. 2A is a cross-section view of another embodiment of the electrochemical gas generator.
Figure 2B:
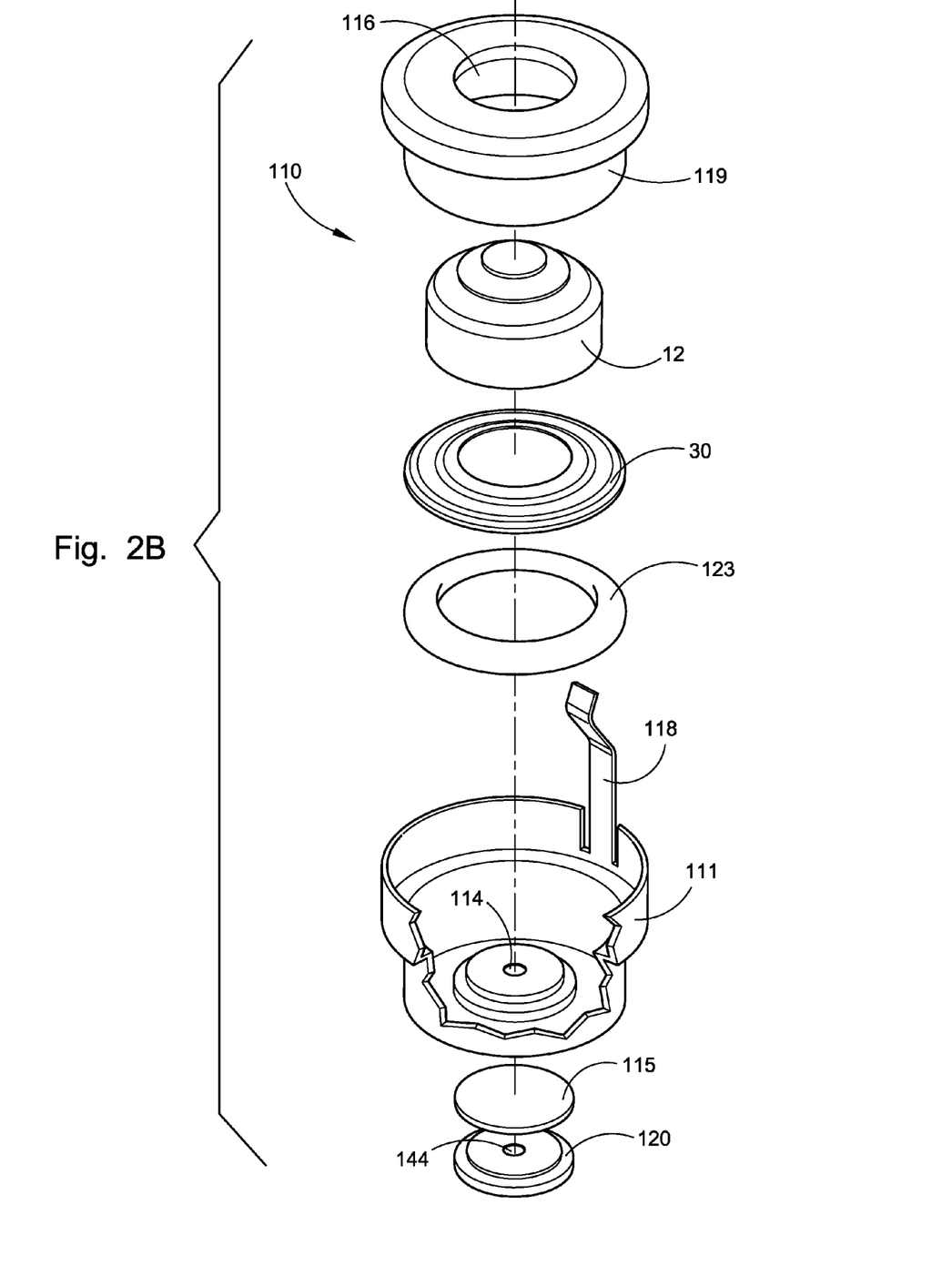
FIG. 2B is an exploded view of the electrochemical gas generator illustrated in FIG. 2A.
Figure 3B:
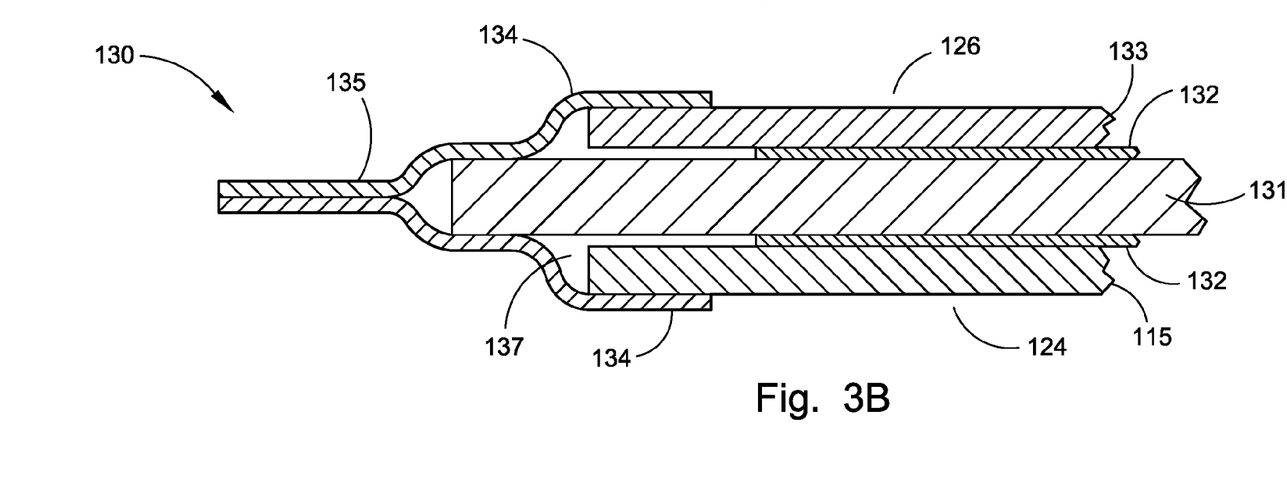
FIG. 3B is a cross-section detailed view of another embodiment of an electrochemical cell assembly which is film-controlled.

FIGS. 2A and 2B, in conjunction with FIGS. 3A and 3B, illustrate a slightly modified version of an autonomous electrochemical oxygen generator which, for oxygen generation, is controlled by an oxygen permeable film, either conductive 115 or non-conductive 125, thereby eliminating the need for the resistor 20 as required in the previously described electrochemical gas generator 10. This electrochemical gas generator 110 is somewhat similar to the previously described electrochemical gas generator 10 in that it has a container 111, with one or more oxygen-containing gas inlets 114 on the bottom and an outlet 116 and activation member 118 on top of the container 111. The oxygen-containing gas inlet 114 and bottom however has an upward extending recess 117 thereat adapted to receive a compression-type fitting 120, such as but not limited to washers, plugs, slugs, and lids, the purpose of which is described later herein. A chamber 113 within the container 111 houses the battery holder 119 and the battery 12.

This electrochemical oxygen generator 110 is film-based and, unlike the previously described current-based electrochemical gas generator 10, is housed below the battery 12 and on the bottom of the container 111. In assembling this generator 110, a sealing ring 123 is placed on the floor [bottom] of the container 111, followed by the electrochemical cell assembly 30, and ending with the battery 12 in its holder 119.

In cases where the electrochemical cell assembly being used is that as illustrated in FIG. 3A, construction is followed by placement of either a conductive oxygen-permeable film 115 or a non-conductive oxygen-permeable film 125 into the recess 117 followed by insertion of the compression-type fitting 120 into the recess and in contact with the conductive oxygen-permeable film 115 or a non-conductive oxygen-permeable film 125. Similar to the previously described generator 10, this is followed by crimping the container 111 inward and downward to achieve an electrical contact between the battery 12 and the electrochemical cell assembly 30 and the container 111.

With the compression-type fitting 120 so pressed into the recess 117 an intact and ready to use film-based electrochemical gas generator 110 is made. A ledge 122 supports the electrochemical cell assembly 30 and, with the sealing ring 123, maintains an air-tight integrity of this electrochemical gas generator 110.

As so configured a large cavity 47 is defined below the electrochemical cell assembly 30 and the floor of the container 111. A small cavity 37 is defined below the electrolytic membrane 31 and the lower segment of the oxygen-impermeable film 34. As will be explained, the large cavity 47 serves an important function to the operation of this film-based electrochemical gas generator 110.

The compression-type fitting 120 should have one or more perforations 144 [one is shown] therein to permit access of air onto the oxygen-permeable film 115, 125. The oxygen-permeable film 115, 125 allows a certain amount of oxygen to diffuse across the oxygen-permeable film 115, 125 and to access the electrochemical cell assembly 30 above. A raised circular ridge 121 on the top of the compression-type fitting 120 defines the active area for oxygen permeation through the oxygen-permeable film 115, 125. The one or more perforations 144 are inside the circular ridge 121 and air for oxygen extraction contacts only the area of the oxygen-permeable film as defined by, and within, the circular ridge 121.

As previously described and illustrated in detail in FIG. 3A, the upper and lower segments of the oxygen impermeable film 34 and the respective outward extensions 35 sandwich the membrane-electrode, current-collector combination 31, 32, and 33 and, with the outward extensions 35, prevents air from circulating around the electrochemical cell assembly 30 but forces oxygen to flow to the electrochemical cell assembly 30 to be processed, with oxygen being released at the discharge side 26 of the electrochemical cell assembly 30 and out of the electrochemical gas generator 110 through its outlet 116, and as a result, the oxygen generation rate is now controlled by oxygen transfer through this oxygen permeable film 115, 125 thereby eliminating the need for the resistor 20.

Figure 4A:
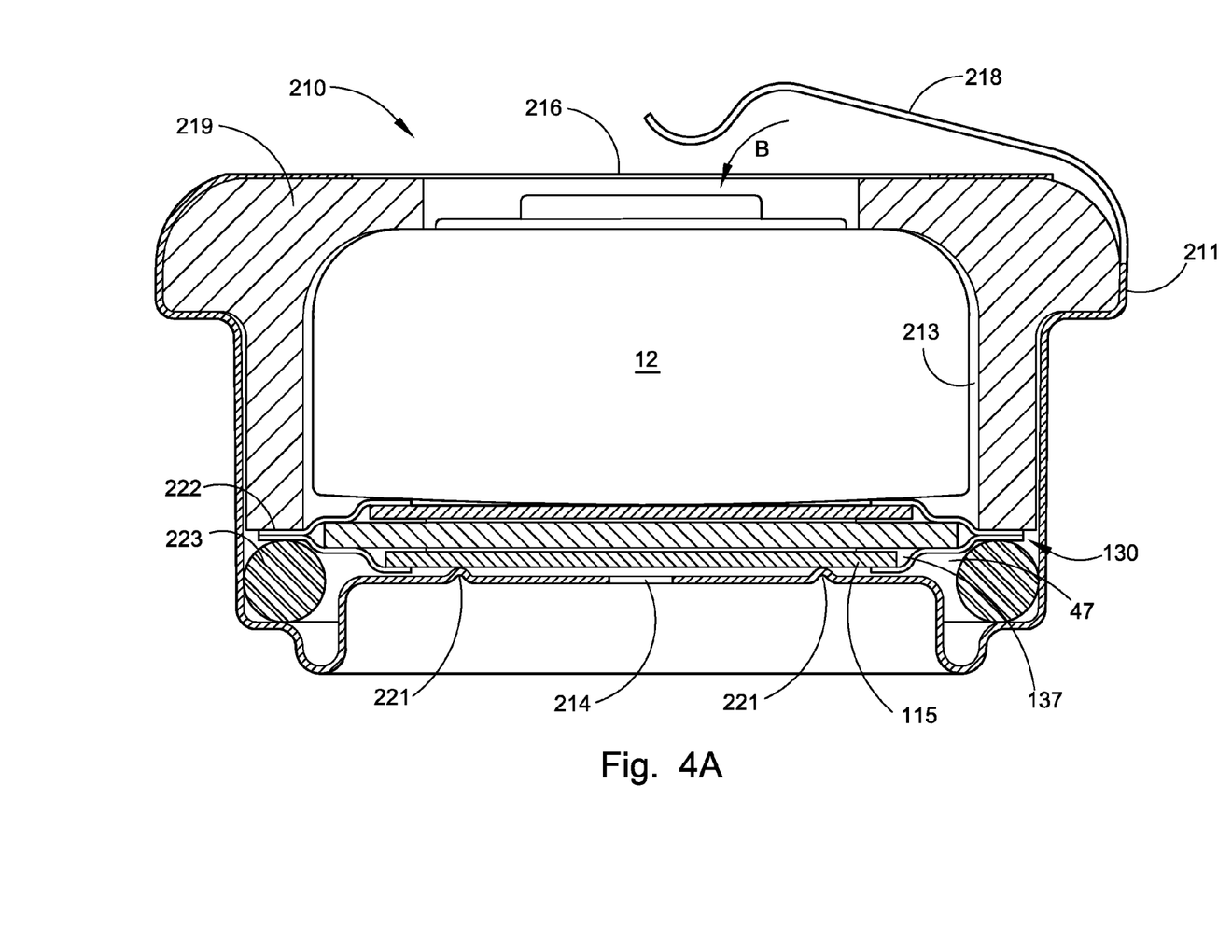
FIG. 4A is a cross-section view of another embodiment of the electrochemical gas generator which is film-controller using conductive film.
Figure 4B:
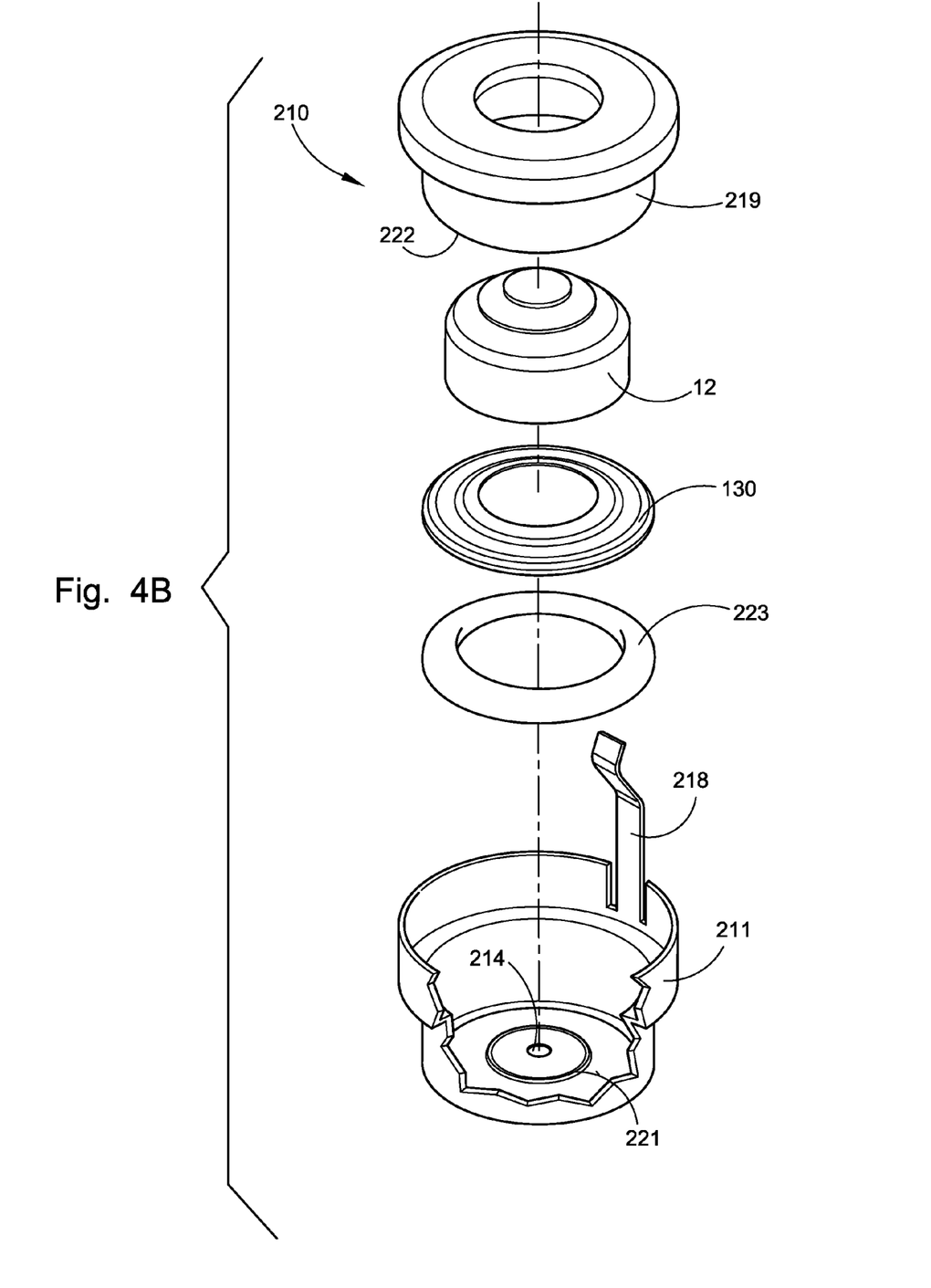
FIG. 4B is an exploded view of the electrochemical gas generator illustrated in FIG. 4A.

In cases where no compression-type fitting 120 is being applied, such as illustrated in FIGS. 4A and 4B [to be described in detail later] the film must be conductive oxygen-permeable 115 as illustrated by the electrochemical cell assembly 130 in FIG. 3B. This embodiment of FIGS. 4A and 4B simplifies the manufacture process and costs associated therewith.

In the embodiment illustrated in FIGS. 2A and 2B, the principle of operation of a film-based, or diffusion-based, oxygen generator eliminates the need for a resistor to control the current and thereby the oxygen generation. Conventionally-available and typical oxygen-permeable film 115, 125 should generally be of a silicone film and more specifically, if it is to be of the non-conductive type, a dimethylsilicone (DMS) film of known oxygen permeability such as produced by Silicone Products, Inc. It is the known permeability of the film which will dictate the quantity of oxygen to be generated and not the strength of the battery 12 rendering battery strength immaterial to its efficiency.

The rate of oxygen transfer through the above-mentioned DMS film 125 is $60 \times 10^{-9}$ cc-cm/cm$^2$-sec-cmHg pressure difference. If a specific oxygen partial pressure difference can be maintained across either type of oxygen-permeable film 115, 125, the oxygen transfer rate will be constant. If the partial pressure of oxygen on the down-stream side of the oxygen-permeable film 115, 125 is small (near zero) the oxygen pressure difference is set at about 16 cm of Hg. The transfer rate of oxygen then becomes equivalent to 0.083 cc-cm/day-cm$^2$. For a film thickness of 10 mils, the rate becomes equivalent to 3.3 cc/day-cm$^2$. To achieve a 1 cc/day transfer rate, the film diameter should generally be 0.6 cm.

To achieve the desired low oxygen pressure on the downstream side of the oxygen-permeable film 115, 125, a battery voltage of 0.9 to 1.7 volts is applied directly to the electrochemical cell assembly 30, without current control.

Each of the film-based generators 110, 210 involve a two stage process for oxygen generation: [1] oxygen diffusion; and [2] electrochemical oxygen concentration.

With regard to the generator 110 illustrated in FIG. 2A, oxygen within the large cavity 47, as defined by the boundaries of the oxygen-permeable film and the electrochemical cell assembly 30 will be immediately scavenged and released as pure oxygen at the cell assembly anode. In fact, applicant has obtained oxygen partial pressures in cavity as low as 100 ppm, or 0.008 cm Hg, a negligible value as compared to 16 cm Hg of oxygen pressure in air.

FIGS. 4A and 4B in conjunction with FIG. 3B illustrates yet another embodiment of an electrochemical gas generator 210 also controlled by an oxygen-permeable film rather than a resistor 20 as previously described for the electrochemical gas generator 10. In this embodiment, however, the oxygen-permeable film must be electrically conductive 115. This electrochemical gas generator 210 is configured similarly to the previously described electrochemical gas generator 110 in that it has a container 211, with one or more inlets 214 on the bottom [one being illustrated for the purpose of allowing entry of an oxygen-containing gas, such as but not limited to, air] and an outlet 216 and activation member 218 on top of the container 211. A chamber 213 within the container 211 houses the battery holder 219 and the battery 12 securely positioned therein. A ledge 222 is defined on the bottom of the battery holder 219. The bottom, or floor, of the container 211 has a raised ridge 221 defining a perimeter thereon having a clearly defined inner side and an outer side. There is no need for the compression-type fitting 120 as in the electrochemical gas generator 110 as previously described.

In assembly of this embodiment, sealing ring 223 is first placed into the container 211 followed by the electrochemical cell assembly 130 [see FIG. 3B], battery 12, and then the battery holder 219. Container 211 is then crimped inward and downward to achieve electrical contact between the battery 12, electrochemical cell assembly 130, and the raised ridge 221. The ledge 222 in combination with the sealing ring 223 supports the electrochemical cell assembly 130 and maintains the required air-tight integrity necessary for the electrochemical gas generator 230 to properly and most efficiently function.

The one or more inlets 214 on the electrochemical gas generator 210 allows free access of any oxygen-containing gas, such as but not limited to, air to the electrochemical cell assembly 130 and the raised ridge 221, defining the active area [inner side of the perimeter] for air access to, and oxygen transfer across, the conductive oxygen-permeable film 115 to the electrolytic membrane 131 and lower electrode 132.

FIG. 3B illustrates in detail the electrochemical cell assembly 130 used in the above described electrochemical gas generator 210. It is similar to the electrochemical cell assembly 30 previously described in that it has solid electrolytic membrane 131 onto which electrodes 132 are embedded on the top and on the bottom of the electrolytic membrane 131. A single current collector 133 is on top of the top electrode 132 and in intimate contact therewith to insure a low resistance electrical contact. A major difference with this electrochemical cell assembly 130 is that the lower current collector 33 as described for the electrochemical cell assembly 30 is replaced by the conductive oxygen-permeable film 115. Electrical conductivity is achieved by the addition of conductive materials to the film such as, but not limited to, carbon, graphite, silver, nickel, or other similarly conductive materials.

This membrane-electrode-film electrochemical cell assembly 130 is partially sandwiched between upper and lower segments of oxygen impermeable film 134 which is used to seal off the edges of electrochemical cell assembly 130 by way of outward extensions 135. As can be seen the oxygen impermeable film 134 sandwiches the membrane-electrode-current collector-film combination 131, 132, 133, 115 and, with the outward extensions 135 in conjunction with the sealing ring 123 [refer to FIGS. 4A and 4B], prevents air from circulating around the electrochemical cell assembly 130 but forces the air to flow to the electrochemical cell assembly 130 from its air intake side 124, to be processed, with oxygen being released at the discharge side 126 of the electrochemical cell assembly 130 and out of the electrochemical gas generator 210 through its outlet 216.

Typical conventionally available components of the electrochemical cell assembly 130 include:
 [1] for the electrolytic member (cation or anion) [131], a typical membrane which is manufactured by DuPont® and known as Nafion®;
 [2] for the electrodes [132], catalytically active materials such as platinum black or platinum activated carbons or graphite;
 [3] for the current collector [133], which typically should be approximately 320 microns thick and less than 5 mm in diameter, porous conductive carbons or graphite paper or porous conductive materials such as conductive silicone rubber or a metal screen;
 [4] for the oxygen permeable film [115], a conductive silicon rubber produced by Silicone Products, Inc., of known oxygen permeability; and
 [5] for the oxygen impermeable film [34] and outward extensions [35], DuPont's® commercially available Kapton® film.

This electrochemical gas generator 210 is activated by moving the activation member 218 in the direction of Arrow B which is then pressed and held in contact with the battery 12. After this movement is completed, the electrochemical cell assembly 130 immediately extracts oxygen from the small cavity 137. Since the oxygen-permeable film 115 is in intimate contact with the lower electrode 132, and because the cavity 137 is extremely small, oxygen pressure in the small cavity 137 in instantly decreased to near zero. This difference in oxygen pressure as contrasted to the air pressure on the intake side 124 of the electrochemical cell assembly 130 becomes the driving force for oxygen transfer across the oxygen-permeable film 115 and subsequent release from the upper electrode [anode] and discharge from the electrochemical gas generator 210 from its outlet 216.

The present disclosure includes that contained in the present claims as well as that of the foregoing description. Although this electrochemical gas generator and cell assemblies have been described in its preferred forms with a certain degree of particularity, it is understood that the present disclosure of the preferred forms has been made only by way of example and numerous changes in the details of construction and combination and arrangement of parts and method steps may be resorted to without departing from the spirit and scope of the electrochemical gas generator and cell assemblies. Accordingly, the scope of the electrochemical gas generator and cell assemblies should be determined not by the embodiment[s] illustrated, but by the appended claims and their legal equivalents.

It must be understood, however, that there may be unforeseeable insubstantial modifications to electrochemical gas generator and cell assemblies that remain as equivalents and thereby falling within the scope of the electrochemical gas generator and cell assemblies described and claimed herein.

What is claimed is:

1. An electrochemical gas generator comprising:
   (a) a container having a chamber within, a top with one or more outlets therein, and a bottom with an upward extending recess and one or more gas inlets on said bottom;
   (b) a battery within said chamber;
   (c) an electrochemical cell assembly below, and in communication with, said battery, said electrochemical cell assembly comprising;
      an electrolytic membrane defining a first outer peripheral edge and a pair of opposing faces,
      a catalytically active electrode above and below said electrolytic membrane,
      a conductive and porous current collector above and below each of said electrodes, each said current collector defining an outwardly-facing face and an inwardly-facing face, with each said current collector inwardly-facing face oriented towards one said opposing membrane face, said current collectors each further defining a second outer peripheral edge, and
      an upper and a lower oxygen-impermeable film, each with an outward extension sealed to one another, and each said film further sealed to one said membrane face as well as one said current collector outwardly-facing face, said upper and lower oxygen-impermeable film above and below and encircling said second peripheral edges and pressing onto each one of said current collectors thereby forming an air-tight seal therearound;
   d) activation means for activating said electrochemical gas generator;
   (e) an oxygen-permeable film of a pre-determined oxygen permeability in said recess; and
   (f) compression means for pressing said oxygen-permeable film into a direct communication with said bottom of said container, said compression means having one or more inlets therein.

2. The electrochemical gas generator of claim 1 wherein said electrolytic membrane is of the cation or anion type.

3. The electrochemical gas generator of claim 1 wherein said compression means is selected from the group consisting of washers, plugs, slugs, and lids.

4. The electrochemical gas generator of claim 1 wherein said oxygen-permeable film is of the conductive or non-conductive type.

5. The electrochemical gas generator of claim 1 further comprising active area means for generating and releasing gases, said active area means encircling said one or more compression means inlets and wherein said one or more gas inlets are above said one or more compression means inlets and further in communication with generated and released gases.

6. The electrochemical gas generator of claim 5 wherein said active area means comprises an upward projecting ridge.

7. An electrochemical gas generator comprising:
   (a) a container having a chamber within, a top with one or more outlets therein, and a bottom with an upward extending recess and one or more inlets on said bottom;
   (b) a battery within said chamber;
   (c) an electrochemical cell assembly below, and in communication with, said battery, said electrochemical cell assembly comprising;
      an electrolytic membrane defining a first outer peripheral edge and a pair of opposing faces,
      a catalytically active upper electrode above said electrolytic membrane,
      a catalytically active lower electrode below said electrolytic membrane,
      a conductive and porous current collector above said upper electrode, said current collector defining an outwardly-facing face and an inwardly-facing face, with said inwardly-facing face oriented towards one said opposing membrane face, said current collector further defining a second outer peripheral edge,
      an oxygen-permeable film of the conductive type and of a pre-determined oxygen permeability below said lower electrode, said oxygen-permeable film defining an outwardly-facing face and an inwardly-facing face, with said inwardly-facing face oriented towards one said opposing membrane face, said oxygen-permeable film further defining a third outer peripheral edge,
      whereby said first peripheral edge extends beyond said second and third peripheral edges, and
      an upper and a lower oxygen-impermeable film, each with an outward extension in sealing communication with one another, wherein said upper oxygen-impermeable film is above and encircling and pressing onto said current collector, and a portion of one of said membrane faces, and said lower oxygen-impermeable film is below and encircling said third peripheral edge and pressing onto said oxygen-permeable film, and a portion of one of said membrane faces, thereby forming an air-tight seal with said current collector, said membrane and said oxygen-permeable film; and
   (d) activation means for activating said electrochemical gas generator.

8. The electrochemical gas generator of claim 7 wherein said electrolytic membrane is of the cation or anion type.

9. The electrochemical gas generator of claim 7 further comprising active area means for generating and releasing gases, said active area means on said bottom and encircling said one or more inlets.

10. The electrochemical gas generator of claim 9 wherein said active area means comprises an upward projecting ridge.

11. An electrochemical gas generator comprising:
   (a) a container having a chamber within, a top with one or more outlets therein, and a bottom with one or more inlets therein;
   (b) a battery within said chamber;
   (c) an electrochemical cell assembly above, and in communication with, said battery, said electrochemical cell assembly comprising:
      an electrolytic membrane defining a first outer peripheral edge and a pair of opposing faces,
      a catalytically active electrode above and below said electrolytic membrane,
      a conductive and porous current collector above and below each of said electrodes, each said current collector defining an outwardly-facing face and an inwardly-facing face, with each said current collector inwardly-facing face oriented towards one said opposing membrane face, said current collectors each further defining a second outer peripheral edge, and
      an upper and a lower oxygen-impermeable film, each with an outward extension sealed to one another, and each said film further sealed to one said membrane face as well as one said current collector outwardly-facing face, said upper and lower oxygen-impermeable film above and below and encircling said second outer peripheral edges and pressing onto each one of said current collectors thereby forming an air-tight seal therearound;
(d) a conductive member in between said battery and said electrochemical cell assembly and in direct communication with said battery and said electrochemical cell assembly;
(e) activation means for activating said electrochemical gas generator; and
(f) current controller means for controlling electric current, said current controller means in communication with said battery and said activation means.

12. The electrochemical gas generator of claim 11 wherein said electrolytic membrane is of the cation or anion type.

13. The electrochemical gas generator of claim 11 wherein said current controller means comprises a resistor.

14. An electrochemical cell assembly comprising:
an electrolytic membrane defining a first outer peripheral edge and a pair of opposing faces;
a catalytically active electrode above and below said electrolytic membrane;
a conductive and porous current collector above and below each of said electrodes, each said current collector defining an outwardly-facing face and an inwardly-facing face, with each said current collector inwardly-facing face oriented towards one said opposing membrane face, said current collectors each further defining a second outer peripheral edge; and
an upper and a lower oxygen-impermeable film, each with outward extension sealed to one another, and each said film further sealed to one said membrane face as well as one said current collector outwardly-facing face, said upper and lower oxygen-impermeable film above and below and encircling said second outer peripheral edges and pressing onto each one of said current collectors thereby forming an air-tight seal therearound.

15. The electrochemical cell assembly of claim 14 wherein said electrolytic membrane is of the cation or anion type.

16. The electrochemical cell assembly of claim 14, wherein said membrane first outer peripheral edge extends beyond said current collectors second outer peripheral edges, such that an outer portion of said pair of opposing membrane faces is exposed for sealing to said upper and a lower oxygen-impermeable film.

17. The electrochemical cell assembly of claim 16, wherein said upper and lower oxygen-impermeable films each define a central aperture formed therethrough to expose portions of said outwardly-facing faces of said current collectors.

18. An electrochemical cell assembly comprising:
an electrolytic membrane defining a first outer peripheral edge and a pair of opposing faces;
a catalytically active upper electrode above said electrolytic membrane;
a catalytically active lower electrode below said electrolytic membrane;
a conductive and porous current collector above said upper electrode, said current collector defining an outwardly-facing face and an inwardly-facing face, with said inwardly-facing face oriented towards one said opposing membrane face, said current collector further defining a second outer peripheral edge;
an oxygen-permeable film of the conductive type and of a pre-determined oxygen permeability below said lower electrode, said oxygen-permeable film defining an outwardly-facing face and an inwardly-facing face, with said inwardly-facing face oriented towards one said opposing membrane face, said oxygen-permeable film further defining a third outer peripheral edge;
whereby said first peripheral edge extends beyond said second and third peripheral edges; and
an upper and a lower oxygen-impermeable film, each with an outward extension in sealing communication with one another, wherein said upper oxygen-impermeable film is above and encircling and pressing onto said current collector, and a portion of one of said membrane faces, and said lower oxygen-impermeable film is below and encircling said third peripheral edge, and pressing onto said oxygen-permeable film, and a portion of one of said membrane faces, thereby forming an air-tight seal with said current collector, said membrane and said oxygen-permeable film.

19. The electrochemical cell assembly of claim 18 wherein said electrolytic membrane is of the cation or anion type.

* * * * *